United States Patent [19]

Wolfram

[11] Patent Number: 4,871,874

[45] Date of Patent: Oct. 3, 1989

[54] PROCESS FOR PRODUCING DIENES

[75] Inventor: Joachim W. Wolfram, Houston, Tex.

[73] Assignee: Ethyl Corporation, Richmond, Va.

[21] Appl. No.: 62,161

[22] Filed: Jun. 15, 1987

[51] Int. Cl.$^4$ .............................................. C07C 87/29
[52] U.S. Cl. ................................... 564/288; 564/486; 585/603; 585/612
[58] Field of Search ................ 585/603, 612; 564/288, 564/486

[56] References Cited

U.S. PATENT DOCUMENTS

| | | | |
|---|---|---|---|
| 1,030,239 | 6/1912 | Hoffman et al. | 585/612 |
| 1,056,814 | 3/1913 | Mercing et al. | 585/612 |
| 1,056,815 | 3/1913 | Mercing et al. | 585/612 |
| 1,056,816 | 3/1913 | Mercing et al. | 585/612 |
| 1,056,817 | 3/1913 | Mercing et al. | 585/612 |
| 2,719,872 | 10/1955 | Happel et al. | 260/678 |
| 3,670,032 | 6/1972 | Romanelli | 260/614 AA |
| 3,932,539 | 1/1976 | Kane | 564/291 |
| 4,188,498 | 2/1980 | Murata et al. | 568/875 |
| 4,266,087 | 5/1981 | Chalk et al. | 568/875 |
| 4,467,118 | 8/1984 | Chalk et al. | 568/687 |
| 4,754,089 | 6/1988 | Matson et al. | 260/684 X |

FOREIGN PATENT DOCUMENTS

| | | |
|---|---|---|
| 247144 | 5/1912 | Fed. Rep. of Germany . |
| 247145 | 5/1912 | Fed. Rep. of Germany . |
| 247271 | 5/1912 | Fed. Rep. of Germany . |
| 247040 | 11/1913 | Fed. Rep. of Germany . |
| 13321 | of 1914 | United Kingdom ............... 585/612 |
| 1107865 | 3/1968 | United Kingdom . |

OTHER PUBLICATIONS

Morrison, T. R. et al., Organic Chemistry, 3rd ed., Allyn and Bacon, Inc., Boston ©1973, pp. 752-753.
Morrison and Boyd, Organic Chemistry, 2nd Ed., 1966, pp. 103, 748-749.
March, Advanced Organic Chemistry: Reactions, Mechanisms, and Structure, McGraw-Hill Book Company, 1968, pp. 758-760.
Babayan et al., Journal of General Chemistry of the USSR, 1955, vol. 25, No. 8, pp. 1567-1570.
Babayan et al., Journal of General Chemistry of the USSR, 1958, vol. 28, No. 5, pp. 1314-1317.
Babayan et al., Journal of General Chemistry of the USSR, 1961, vol. 31, No. 2, pp. 562-566, 752-757, 758-761.
Babayan et al., Journal of General Chemistry of the USSR, 1963, vol. 33, No. 5, pp. 1720-1726.
Noller, Chemistry of Organic Compounds, W. B. Saunders Company, Philadelphia and London, 3rd Edition, 1965, p. 778.
Dang et al., Tetrahedron Letters, 1978, No. 2, pp. 191-194.
Tanaka et al., J. Am. Chem. Soc., 1975, vol. 97, pp. 3252-3254.
Tsuji et al., Tetrahedron Letters, 1978, No. 24, pp. 2075-2078.
Cocker et al., J. Chem. Soc., Perkin Trans., 1984, I, pp. 2245-2254.
Beger et al., Journal f. prakt, Chemie, Band 326, Heft 1, 1984, pp. 12-22.
Guseinova et al., Higher Institutes of Learning, Chemistry and Chemical Technology, 1984, vol. 27(8), pp. 890-895.
Chemical Abstracts, 1986, Issue 22, p. 2, Abstract 105:133553r.
Short, J. Org. Chem., 1972, vol. 37, No. 13, pp. 2201-2202.
House, Modern Synthetic Reactions, W. A. Benjamin Inc., 1972, pp. 478-491.

Primary Examiner—Patrick P. Garvin
Assistant Examiner—George R. Fourson
Attorney, Agent, or Firm—John F. Sieberth

[57] ABSTRACT

Alkadienes are produced by reacting alkenyltrialkylammonium halide in which the double bond is allylic or homoallylic relative to the nitrogen atom with a strong inorganic base under phase transfer conditions. In this reaction trialkylamine is eliminated from the quaternary ammonium halide thereby resulting in the concurrent formation of the alkadiene. Long chain (e.g., $C_6$–$C_{20}$) conjugated alkadienes, can readily be prepared from the corresponding alkenes in good yields on an economical basis by a three-stage process involving:

(a) allylically monobrominating an alkene in the liquid phase;
(b) converting the allylically monobrominated alkene into alkenyl quaternary ammonium bromide by reaction with a trialkyl amine; and
(c) reacting the alkenyl quaternary ammonium bromide with a strong inorganic base under phase transfer conditions so that conjugated alkadiene and trialkylamine are formed.

23 Claims, No Drawings

PROCESS FOR PRODUCING DIENES

FIELD

This invention relates to the production of dienes, e.g., hydrocarbons having conjugated double bonds in an aliphatic chain. In a more particular embodiment, this invention relates to a process for converting alkenes, i.e., acyclic hydrocarbons having one olefinic double bond in the molecule, into alkadienes.

BACKGROUND

Various methods have been investigated for the synthesis of dienes. These include:

Acid-catalyzed dehydration of 1, 2-, 1,3-, or 1,4-diols. Note for example, Noller, *Chemistry of Organic Compounds*, W. B. Saunders Company, Philadelphia and London, 3rd Edition, 1965, page 778.

Coupling of vinyl halides with various vinyl metal reagents catalyzed by transition metal compounds. See for example Dang et al., *Tetrahedron Letters*, 1978, pages 191–194 and references cited therein.

Formation from allylic alcohols via oxirane and enediol. Tanaka et. al., *J. Am. Chem. Soc.*, 1975, 97, pages 3252–3254.

Palladium catalyzed elimination reactions using allylic acetates and allylic phenyl ethers. Tsuji et al., *Tetrahedron Letters*, 1978, No. 24, pages 2075–2078.

Base-catalyzed thermal decomposition of methohydroxides and methodeutero-oxides of various 5-N,N-dimethylamino-pent-1-enes. Cocker et al., *J. Chem. Soc., Perkins Trans.*, 1984, I, pages 2245–2254.

U. S. Pat. No. 4,467,118, to Chalk et al., describes conversion of tertiary allylic amines to dienes via a zero valent palladium phosphine complex and a weak acid.

In *Journal f. prakt. Chemie*, Band 326, Heft 1, 1984, pages 12–22, Beger et al. report that a product containing 1,3-alkadiene was produced from the reaction of 1,2-dihaloalkanes and N-methyldicyclohexylamine. The product also contained cis and trans-1-halo-1-alkenes, 2-halo-1-alkene, the 2,4-diene and the 1-alkene.

Still other methods for the synthesis of alkadienes have previously been reported.

Babayan, Vartanyan and Zurabov, *Journal of General Chemistry of the USSR*; (in English Translation), 1955, Vol. 25, No. 8, pages 1567–1570 indicate that treatment of quaternary ammonium compounds containing the 3-chlorobutenyl radical with aqueous NaOH yields chloroprene.

Babayan, Mkrian and Giuli-Kevkhian, ibid, 1958, Vol. 28, No. 5, pages 1314–1317, report the preparation of isoprene by alkaline cleavage of quaternary ammonium salts obtained by reaction of $\alpha,\beta$- and $\gamma,\gamma$-dimethylallyl chlorides with tertiary amines. Hot aqueous NaOH was used to effect the cleavage reaction.

In the same journal, 1961, Vol. 31, No. 2, pages 752–757, Babayan and Martirosyan again refer to alkaline cleavage of quaternary ammonium salts containing 3-chlorobuten-2-yl radicals to form chloroprene and vinylacetylene, and to the formation of isoprene by alkaline cleavage of quaternary ammonium salts containing the 3-methylbuten-2-yl radical ($\gamma,\gamma$-dimethylallyl radical).

In an ensuing paper, ibid, 1961, Vol. 31, No. 2, pages 758–761, Babayan and Martirosyan report on a study, inter alia, of the effect of a methyl group in the $\gamma$-position of various haloalkyl-containing quaternary ammonium salts treated with alcoholic alkali.

And, in the same journal, 1961, Vol. 31, No. 2, pages 562–566, Babayan, Gegelyan and Indzhikyan show that the introduction of methyoxymethyl substituents in the $\delta$-position to $\beta,\gamma$-unsaturated groups of quaternary ammonium salts facilitates the reaction of their splitting under the influence of aqueous alkali. As Babayan, Indzhikyan, Grigoryan and Minasyan, ibid, 963. Vol. 33, No. 5, pages 1720–1726, point out, those results agree with the idea that the step which determines the rate of the reaction of alkaline splitting of quaternary ammonium salts with $\beta,\gamma$-unsaturated groups is the removal of a proton from the position to the nitrogen. Accordingly, the 1963 paper reports the results of an extension of this idea —positioning of a phenyl or para-substituted phenyl group in the $\delta$-position to the nitrogen in the $\beta,\gamma$-unsaturated groups in order to take advantage of the "great protonizing action of the phenyl group".

In the case of the Babayan et al. process for producing isoprene from a quaternary ammonium salt containing an $\gamma,\gamma$-dimethylallyl group (i.e., a 3-methylbuten-2-yl group), the reactant contains no less than six extractable protons (two methyl groups) in the 4-position relative to the nitrogen atom.

THE INVENTION

In accordance with this invention it has been found possible to convert monoolefinic quaternary ammonium halides into dienes even though there are no activating groups such as phenyl, p-nitrophenyl, halogen, or methoxymethyl positioned adjacent or even in proximity to the carbon atom to be protonized, and even though the quaternary ammonium halide contains a monoolefinic group containing only two hydrogen atoms (extractable protons) in the 4-position relative to the nitrogen atom. In fact, the preferred quaternary ammonium halides used in the process have no activating group and little if any branching anywhere in the alkenyl chain.

More particularly, dienes are produced by reacting alkenyltrialkylammonium halide with a strong inorganic base in an aqueous system under phase transfer conditions. In this reaction trialkylamine is eliminated from the quaternary ammonium halide thereby resulting in the concurrent formation of an alkadiene. Preferably the alkenyltrialkylammonium halide will have an allylic or homoallylic double bond. Alkenyltrialkylammonium halides having an allylic double bond are the most preferred reactants as they are readily prepared and form 1,3-conjugated alkadienes in good yields.

While the aqueous system may contain various inert organic solvents such as ethers, amines or the like, the reaction is preferably conducted in the presence of a phase transfer catalyst in a reaction medium composed of inert hydrocarbon and water. Various hydrocarbons can be used in these mixed phase systems including liquid paraffins, cycloparaffins and aromatics. Particularly desirable hydrocarbons for this use are the mononuclear aromatic hydrocarbons such as toluene, xylene, mesitylene, ethyl benzene, and the like. Any of a variety of phase transfer catalysts may be used in the process, including crown ethers, etc. While operable, it is preferred however not to employ quaternary ammonium compounds for this purpose as they tend to participate in analogous reactions and thereby produce products containing additional impurities. For best results, use should be made of polyalkylene glycols, most preferably polyethylene glycols, as the phase transfer catalyst.

Amounts of phase transfer catalysts used in the process may be varied to a considerable extent. Ordinarily from about 0.5 to about 25 and preferably from about 1 to about 5 weight percent based on the quaternary ammonium halide will be used. On a laboratory scale, approximately 10 percent by weight of a polyethylene glycol phase transfer catalyst has been found efficacious.

A wide variety of alkenyltrialkylammonium halides may be employed in the process. Preferably the alkenyl group will contain from about 6 to about 20 carbon atoms and its double bond will be allylic or homoallylic relative to the nitrogen atom. The alkenyl group may be linear or branched in character, but preferably will be free of branching in the 4-position relative to the nitrogen atom. It will be understood that even longer chain alkenyl groups may be present in the alkenyltrialkylammonium halide reactant. In accordance with a preferred embodiment of this invention, the alkenyltrialkylammonium halide reactant is a 1-alk-2-enyltrialkylammonium halide or a 3-alk-1-enylalkylammonium halide, or a mixture of both of these materials. The alkyl groups of the alkenyltrialkylammonium halide groups may likewise vary to a considerable extent from short chain to long chain and from linear to branched chain. Moreover, the alkyl group may be substituted with inert substituents such as alkoxy groups and the like. Preferably however, the alkyl groups of the alkenyltrialkylammonium halide reactant are free of beta-hydrogen atoms as this reduces the likelihood of product contamination which might otherwise occur due to conversion of the alkyl groups to olefin. The halogen atom of the alkenyltrialkylammonium halide is preferably chlorine and most preferably bromine, although compounds of the other halogens may prove feasible.

The following alkenyltrialkylammonium halides serve to illustrate the wide variety of materials which may be subjected to the process in accordance with this invention:
1-oct-2-enyltrimethylammonium bromide
3-oct-1-enyltrimethylammonium bromide
4-oct-2-enyltrimethylammonium bromide
2-oct-3-enyltrimethylammonium bromide
4-methyl-1-hex-2-enyltriethylammonium bromide
6,6-dimethyl-3-oct-1-enyltributylammonium chloride
1-hept-3-enyltrioctylammonium iodide
4,6-dimethyl-3-hept-1-enylcyclohexyldimethylammonium bromide
2,2,4-trimethyl-1-pent-3-enyltrimethylammonium chloride
1-octacos-2-enyltrimethylammonium chloride
3-hexatriacont-1-enyltrimethylammonium bromide
13-phenyl-3-tridec-1-enyldimethylneopentylammonium chloride.

Exemplary of the preferred alkenyltrialkylammonium halides which may be used in the process either singly or in appropriate mixtures are:
1-hex-2-enyltrimethylammonium bromide
3-hex-1-enyltrimethylammonium bromide
1-hex-2-enyltrimethylammonium chloride
3-hex-1-enyltrimethylammonium chloride
1-hept-2-enyltrimethylammonium bromide
3-hept-1-enyltrimethylammonium bromide
1-hept-2-enyltrimethylammonium chloride
3-hept-1-enyltrimethylammonium chloride
1-oct-2-enyltrimethylammonium bromide
3-oct-1-enyltrimethylammonium bromide
1-oct-2-enyltrimethylammonium chloride
3-oct-1-enyltrimethylammonium chloride
1-dec-2-enyltrimethylammonium bromide
3-dec-1-enyltrimethylammonium bromide
1-dec-2-enyltrimethylammonium chloride
3-dec-1-enyltrimethylammonium chloride
1-dodec-2-enyltrimethylammonium bromide
3-dodec-1-enyltrimethylammonium bromide
1-dodec-2-enyltrimethylammonium chloride
3-dodec-1-enyltrimethylammonium chloride
1-tetradec-2-enyltrimethylammonium bromide
3-tetradec-1-enyltrimethylammonium bromide
1-tetradec-2-enyltrimethylammonium chloride
3-tetradec-1-enyltrimethylammonium chloride
1-hexadec-2-enyltrimethylammonium bromide
3-hexadec-1-enyltrimethylammonium bromide
1-hexadec-2-enyltrimethylammonium chloride
3-hexadec-1-enyltrimethylammonium chloride
1-octadec-2-enyltrimethylammonium bromide
3-octadec-1-enyltrimethylammonium bromide
1-octadec-2-enyltrimethylammonium chloride
3-octadec-1-enyltrimethylammonium chloride
1-eicos-2-enytrimethylammonium bromide
3-eicos-1-enyltrimethylammonium bromide
1-eicos-2-enytrimethylammonium chloride
3-eicos-1-enyltrimethylammonium chloride
1-non-2-enyltrineopentylammonium bromide
1-undec-2-enyltriethoxymethylammonium chloride
3-tridec-1-enyldimethylneopentylammonium The preferred strong inorganic bases used in the process are sodium hydroxide and potassium hydroxide. These may be formed in situ by the addition to the reaction system of sodium oxide or potassium oxide. Other strong inorganic bases which may be used include lithium hydroxide, calcium hydroxide, strontium hydroxide, barium hydroxide, and the like. For best results, the amount of inorganic base should be in excess of the stoichiometric amount required to react with the halogen contained in the alkenyltrialkylammonium reactant. Generally speaking, excess amounts as high as fifteen times theoretical are entirely satisfactory.

Reaction temperatures used in the process should of course be sufficiently high as to cause the desired reaction to occur and this may vary from case to case depending for example upon the identity of the alkenyltrialkylammonium reactant and the inorganic base employed. Naturally, such additional factors as the boiling point or boiling range of the liquid phase reaction medium and the prevailing pressure under which the reaction is being conducted are also factors that will be taken into consideration in selecting the reaction temperature. In general temperatures falling within the range of from about 50° to about 200° C. are preferred although departures from this range are permissible. The reaction may be conducted under pressure in a sealed reactor using low boiling solvent as well.

The trialkylamine liberated in the process is preferably recovered, for example, by stripping, distillation, solvent extraction or other known procedures, so that it is available for use in reaction with alkenyl halide to form additional alkenyltrialkylammonium halide reactant. When conducting the process on a continuous or semi-continuous basis using the preferred alkenyltrimethylammonium halides, the liberated trimethylamine is readily stripped from the reaction product for return as recycle to the reactor in which the alkenyltrimethylammonium halide reactant is produced.

This invention makes it commercially feasible to produce long chain (e.g., $C_6$-$C_{20}$) alkadienes, including conjugated alkadienes, from the corresponding alkenes in good yields on a economical basis. In the case of conjugated alkadienes (the preferred products), this is accomplished by a three-stage process involving:

(a) allylically monobrominating an alkene, preferably a 1-alkene, in the liquid phase;
(b) converting the allylically monobrominated alkene into alkenyl quaternary ammonium bromide by reaction with a trialkyl amine; and
(c) reacting the alkenyl quaternary ammonium bromide with a strong inorganic base under phase transfer conditions so that conjugated alkadiene and trialkylamine are formed.

Procedures for conducting the allylic bromination of (a) above have been reported heretofore in the literature. See for example H. O. House, *Modern Synthetic Reactions*, W. A. Benjamin, Inc., pages 478–491, especially page 485. Conversion of the allylic bromide into quaternary ammonium bromides in (b) above is readily effected by simply intermixing the allylic bromide and the trialkylamine such as is shown in Example II hereinafter. The presence of the allylic double bond in the alkenyl bromide tends to accelerate reaction rate as compared to use of alkyl bromides in the reaction. Thus it is desirable to control reaction temperature to prevent excessive heat formation.

The practice and advantages of this invention will become still further apparent from a consideration of the ensuing illustrative examples.

EXAMPLE I

Allylic Monobromination of 1-Alkene

To a reactor containing cyclohexane solvent is charged 1.5 equivalents of 1-decene, and ozone is passed through the solution until a 300–400 ppm concentration of 1-decene ozonide is achieved. The reaction mixture is heated to 80° C. and solid dibromodimethylhydantoin added incrementally such that the temperature stays in the 75°–80° C. range until 1.0 equivalent (0.5 moles per mole of 1-decene) has been added. Heating at 80° C. is continued for an additional 30 minutes and then the slurry is cooled to room temperature. With a total reaction time of three hours, the yield of the desired allylically brominated decenes (3-bromodecene and 1-bromo-2-decene) was 72% at 75% conversion. The yield of by-product 1,2-dibromodecane was 8.3% at 75% conversion. Workup of the reaction mixture involves centrifuging to remove and recover the 5,5-dimethylhydantoin. The filter cake is then washed with a small amount of 1-decene which may be combined with the centrifugate for use in the procedure of Example II.

EXAMPLE II

Formation of Alkenyltrialkylammonium Bromide

The organic centrifugate from Example I (composed primarily of 1-bromo-2-decene in 1-decene) is charged into a reaction vessel. A solution of 25 weight percent trimethylamine in water is added at such a rate that the reaction temperature is maintained below 50° C. until one equivalent of trimethylamine has been added (70% of 1-decene originally charged in Example I). The reaction requires three hours. The yield for this reaction is 86 percent based on 1-bromo-2-decene and 3-bromo-1-decene. The reaction mixture is allowed to stand for thirty minutes to achieve good phase separation. The aqueous phase contains the desired intermediate product 1-dec-2-enyltrimethylammonium bromide and 3-dec-1-enyltrimethylammonium bromide (collectively called "TMDA Bromide"). The aqueous phase is separated for use in the procedure of Example III and the organic phase is distilled to recover unreacted 1-decene and 1,2-dibromodecane.

EXAMPLE III

Conjugated Alkadiene Production

The aqueous layer from Example II containing the TMDA bromide is charged into a reaction vessel along with an equal volume of toluene. Solid sodium hydroxide (10 equivalents based on TMDA bromide) is added along with 10 weight percent of PEG 600 phase transfer catalyst (also based on TMDA bromide). The reaction mixture is refluxed for five hours then cooled. The organic phase contains 1,3-decadiene (90 percent yield based on TMDA bromide) in toluene. The trimethylamine formed during the reaction may be recovered by bubbling the vent gases through water as the reaction proceeds. After cooling to room temperature, agitation is stopped and the phases allowed to separate. The organic phase contains 1,3-decadiene in toluene. The aqueous phase contains sodium bromide, excess sodium hydroxide and any remaining trimethylamine. The upper organic phase is isolated and distilled. The organic phase is solvent stripped to remove toluene, and then distilled under reduced pressure to isolate 1,3-decadiene (boiling point 170° C. at 760 mm Hg, 85° C. at 40 mm Hg).

In contrast to the results shown in Example III, on refluxing TMDA bromide with excess potassium hydroxide in a mixed phase system of toluene and water without any phase transfer catalyst, the yield of 1,3-decadiene (as determined by gas chromatography using undecane as an internal standard) after 5 hours was 62 percent. When an attempt was made to run the same reaction at a higher temperature (150° C.) in tetraglyme as solvent and with excess powdered sodium hydroxide as the base, the yield of 1,3-decadiene was only 15 percent, the main product being an $\alpha,\beta$-unsaturated aldehyde.

It will be appreciated of course that Example III exemplifies the preferred mode of carrying out the unitary alkadiene production process of this invention and that the alkenyltrimethylammonium bromide used as the raw material in such process may be produced by methods other than those described in Examples I and II. Nevertheless, the procedures given in Examples I and II represent the best modes currently contemplated for carrying out those steps and thus taken together the three Examples represent the best mode presently contemplated for carrying out the embodiment of this invention involving conversion of 1-alkenes into 1,3-alkadienes.

As is well known, alkadienes, especially 1,3-alkadienes, can be used in the synthesis of various products. For example, these dienes may be homopolymerized using procedures reported by or referred to in G. Natta et al., *Chim. Ind. (Milan)*, 46 (10), pages 1158–1164 (1964; Ciampelli et al., *J. Polymer Sci.*, Part C, No. 7, pages 213–218 (1964); Ciampelli et al., Ibid, pages 219–224 (1964); U. S. Pat. Nos. 3,194,799 to Coover, Jr.; and 4,575,538 to Hsieh et al. Copolymers of ethylene and non-conjugated dienes such as 1,5-hexadiene may be formed by the method described by Makowski et al., *J. Polymer Sci., Part A*, 2(11), pages 4973–4987 (1964). Likewise, dienes may be used in the formation of copolymers, both random copolymers and block copolymers, with vinyl aromatics such as styrene and the like. See for example Belgium Patent No. 661,095 (1965). The dienes formed by the process of this invention may also be oligomerized to form drying oils, tackifiers and the like. U. S. Pat. No. 2,429,582 to Morris et al., illustrates one method which may be used to form such oligomers. Dienes are also useful as raw materials for the synthesis of diepoxides, tetrahaloalkanes, and various other end products. Conjugated dienes are of particular utility as reactants in the well-known Diels-Alder synthesis reaction with dienophiles such as maleic anhydride, dimethylacetylene dicarboxylate, and many others.

What is claimed is:

1. A process of producing alkadiene which comprises reacting alkenyltrialkylammonium halide in which the double bond is allylic or homoallylic relative to the nitrogen atom with a strong inorganic base in the presence of a phase transfer catalyst in a reaction medium composed of inert hydrocarbon and water so that alkadiene and trialkylamine are formed.

2. A process of claim 1 wherein the phase transfer catalyst is a polyethylene glycol.

3. A process of claim 1 wherein the alkenyl group of the alkenyltrialkylammonium halide contains at least 6 carbon atoms and is free from branching in the 4-position.

4. A process of claim 1 wherein the alkyl groups of the alkenyltrialkylammonium halide are free of beta-hydrogen atoms.

5. A process of claim 1 wherein the alkenyltrialkylammonium halide is an alkenyltrialkylammonium bromide.

6. A process of claim 1 wherein the alkenyltrialkylammonium halide is an alkenyltrialkylammonium bromide in which the alkyl-groups are free of beta-hydrogen atoms, and wherein the phase transfer catalyst is a polyethylene glycol.

7. A process of claim 1 wherein the double bond of the alkenyltrialkylammonium halide is allylic relative to the nitrogen atom.

8. A process of claim 7 wherein the alkenyltrialkylammonium halide is an alkenyltrialkylammonium bromide.

9. A process of producing alkadiene which comprises heating alkenyltrimethylammonium bromide in which the double bond is allylic or homoallylic relative to the nitrogen atom with excess sodium hydroxide or potassium hydroxide in the presence of a polyalkylene glycol phase transfer catalyst in a mixed phase liquid reaction medium composed of inert hydrocarbon and water so that alkadiene and trimethylamine are formed.

10. A process of claim 9 performed in a refluxing reaction medium comprising water and toluene.

11. A process of claim 9 wherein the phase transfer catalyst is a polyethylene glycol.

12. A process of claim 9 wherein the trimethylamine is recovered and reacted with alkenylbromide to form additional alkenyltrimethylammonium bromide for use in the process of claim 9.

13. A process of claim 9 wherein the alkenyltrimethylammonium bromide is a 1-alk-2-enyltrimethylammonium bromide or a 3-alk-I-enyltrimethylammonium bromide or a mixture of 1-alk-2-enyl-trimethylammonium bromide and 3-alk-1-enyltrimethylammonium bromide.

14. A process of claim 9 wherein the alkenyltrimethylammonium bromide is a 1-alk-2-enyltrimethylammonium bromide or a 3-alk-1-enyltrimethylammonium bromide or a mixture of 1-alk-2enyltrimethylammonium bromide and 3-alk-1-enyltrimethylammonium bromide, wherein the reaction is performed in a refluxing reaction medium comprising water and toluene and wherein the phase transfer catalyst is a polyethylene glycol.

15. A process of producing conjugated alkadiene which comprises
(a) allylically monobrominating an alkene in the liquid phase;
(b) converting the allylically monobrominated alkene into alkenyl quaternary ammonium bromide by reaction with a trialkyl amine; and
(c) reacting the alkenyl quaternary ammonium bromide with a strong inorganic base under phase transfer conditions so that conjugated alkadiene and trialkylamine are formed.

16. A process of claim 15 wherein the alkyl groups of said trialkylamine are free of beta-hydrogen atoms and wherein the alkenyl group of said alkenyl quaternary ammonium bromide is free of branching in the 4-position.

17. A process of claim 15 wherein the strong inorganic base is sodium hydroxide or potassium hydroxide.

18. A process of claim 15 wherein the alkene of (a) is a 1-alkene.

19. A process of claim 15 wherein the trialkylamine is trimethyl amine, wherein the strong inorganic base is sodium hydroxide or potassium hydroxide and wherein the reaction of (c) is conducted in the presence of a polyalkylene glycol phase for catalyst in a mixed phase liquid reaction medium composed of inert hydrocarbon and water.

20. A process of claim 19 wherein the phase transfer catalyst is a polyethylene glycol.

21. A process of claim 20 wherein the reaction of (c) is performed in a refluxing reaction medium comprising water and toluene 22. A process of claim 20 wherein trimethylamine formed in (c) is recycled to (b).

23. A process of claim 20 wherein the alkene is a 1-alkene containing from about 6 to about 20 carbon atoms in the molecule and is free of branching in the 4-position.

* * * * *